US008273347B2

(12) United States Patent
Attawia et al.

(10) Patent No.: US 8,273,347 B2
(45) Date of Patent: Sep. 25, 2012

(54) AUTOLOGOUS TREATMENT OF DEGENERATED DISC WITH CELLS

(75) Inventors: Mohamed Attawia, Canton, MA (US); Hassan Serhan, South Easton, MA (US); Thomas M. DiMauro, Southboro, MA (US); Melissa Grace, Raynham, MA (US); David Urbahns, Barrington, RI (US)

(73) Assignee: DePuy Spine, Inc., Raynham, MA (US)

( * ) Notice: Subject to any disclaimer, the term of this patent is extended or adjusted under 35 U.S.C. 154(b) by 768 days.

(21) Appl. No.: 10/714,594

(22) Filed: Nov. 14, 2003

(65) Prior Publication Data

US 2004/0229786 A1 Nov. 18, 2004

Related U.S. Application Data

(63) Continuation-in-part of application No. 10/714,559, filed on Nov. 13, 2003, now abandoned, which is a continuation-in-part of application No. 10/631,487, filed on Jul. 31, 2003, which is a continuation-in-part of application No. 10/610,355, filed on Jun. 30, 2003, now Pat. No. 7,429,378, which is a continuation-in-part of application No. 10/456,948, filed on Jun. 6, 2003, now Pat. No. 7,344,716.

(60) Provisional application No. 60/470,098, filed on May 13, 2003.

(51) Int. Cl.
*A61K 35/28* (2006.01)
*A61K 38/18* (2006.01)

(52) U.S. Cl. ........................ 424/93.7; 514/8.9
(58) Field of Classification Search ................ None
See application file for complete search history.

(56) References Cited

U.S. PATENT DOCUMENTS

| | | |
|---|---|---|
| 3,678,158 A | 7/1972 | Sussman |
| 4,341,867 A | 7/1982 | Johansen |
| 4,427,649 A | 1/1984 | Dingle et al. |
| 4,435,506 A | 3/1984 | Jackson et al. |
| 4,696,816 A | 9/1987 | Brown |
| 5,095,037 A | 3/1992 | Iwamitsu et al. |
| 5,116,964 A | 5/1992 | Capon et al. |
| 5,194,596 A | 3/1993 | Tischer et al. |
| 5,223,248 A | 6/1993 | McNamara et al. |
| 5,225,538 A | 7/1993 | Capon et al. |
| 5,231,024 A | 7/1993 | Moeller et al. |
| 5,258,371 A | 11/1993 | Golub et al. |
| 5,270,300 A | 12/1993 | Hunziker |
| 5,368,841 A | 11/1994 | Trauner et al. |
| 5,447,851 A | 9/1995 | Beutler et al. |
| 5,510,370 A | 4/1996 | Hock |
| 5,602,156 A | 2/1997 | Kohn et al. |
| 5,656,272 A | 8/1997 | Le et al. |
| 5,656,644 A | 8/1997 | Adams et al. |
| 5,728,396 A | 3/1998 | Peery et al. |
| 5,827,886 A | 10/1998 | Hersh |
| 5,833,984 A | 11/1998 | Eibl et al. |
| 5,842,477 A | 12/1998 | Naughton et al. |
| 5,942,499 A | 8/1999 | Radomsky |
| 5,965,583 A | 10/1999 | Beers et al. |
| 6,015,557 A | 1/2000 | Tobinick et al. |
| 6,049,026 A | 4/2000 | Muschler |
| 6,228,062 B1 | 5/2001 | Howell et al. |
| 6,277,969 B1 | 8/2001 | Le et al. |
| 6,284,471 B1 | 9/2001 | Le et al. |
| 6,294,170 B1 | 9/2001 | Boone et al. |
| 6,300,347 B1 | 10/2001 | Revesz |
| 6,340,369 B1 | 1/2002 | Ferree |
| 6,352,557 B1 | 3/2002 | Ferree |
| 6,419,944 B2 | 7/2002 | Tobinick |
| 6,541,477 B2 | 4/2003 | Goehring et al. |
| 6,554,830 B1 | 4/2003 | Chappius |
| 6,590,081 B1 | 7/2003 | Zhang |
| 6,593,310 B1 | 7/2003 | Cullis-Hill |
| 6,623,472 B1 | 9/2003 | Reinecke et al. |
| 6,713,246 B1 | 3/2004 | Reinecke et al. |
| 6,756,215 B1 | 6/2004 | Wolfraim et al. |
| 7,067,144 B2 | 6/2006 | Demopulos et al. |
| 7,344,716 B2 | 3/2008 | DiMauro et al. |
| 7,429,378 B2 | 9/2008 | Serhan et al. |
| 7,553,827 B2 | 6/2009 | Attawia et al. |
| 7,799,782 B2 | 9/2010 | Munson et al. |
| 8,067,397 B2 | 11/2011 | Attawia et al. |
| 2001/0006948 A1 | 7/2001 | Kang et al. |
| 2001/0016195 A1 | 8/2001 | Tobinick |
| 2001/0026801 A1 | 10/2001 | Tobinick |
| 2002/0010471 A1 | 1/2002 | Wironen et al. |
| 2002/0019351 A1 | 2/2002 | Ke et al. |
| 2002/0026244 A1 | 2/2002 | Trieu |

(Continued)

FOREIGN PATENT DOCUMENTS

AU 2003263340 A1 3/2004

(Continued)

OTHER PUBLICATIONS

Crevenstein et al (2004). Annals of Biomedical Engineering. 32, 430-434.*
Tanney et al (1980). Applied and Environmental microbiology. p. 269-273.*
Raucci et al (2004). JBC. 279, 1747-1756.*
McMillan et al (2002). Transfusion and Apheresis Science. 27, 73-81.*
Khoury et al. (1991). AJR. 157, 685-691.*

(Continued)

*Primary Examiner* — Robert C Hayes

(74) *Attorney, Agent, or Firm* — Hamilton, Brook, Smith & Reynolds, P.C.

(57) ABSTRACT

The present invention relates to administering autologous uncultured cells into a diseased intervertebral disc.

39 Claims, No Drawings

U.S. PATENT DOCUMENTS

| | | | |
|---|---|---|---|
| 2002/0032155 A1 | 3/2002 | Ferree |
| 2002/0082697 A1 | 6/2002 | Damien |
| 2002/0107200 A1 | 8/2002 | Chang et al. |
| 2002/0169162 A1 | 11/2002 | Smith et al. |
| 2002/0198599 A1 | 12/2002 | Haldimann |
| 2003/0007972 A1 | 1/2003 | Tobinick |
| 2003/0039651 A1 | 2/2003 | Olmarker |
| 2003/0049256 A1 | 3/2003 | Tobinick |
| 2003/0069639 A1 | 4/2003 | Sander et al. |
| 2003/0134792 A1 | 7/2003 | Pike et al. |
| 2003/0207827 A1 | 11/2003 | Boyle et al. |
| 2003/0220692 A1 | 11/2003 | Shapiro et al. |
| 2003/0235585 A1 | 12/2003 | Fischkoff et al. |
| 2004/0022864 A1 | 2/2004 | Freyman et al. |
| 2004/0126372 A1 | 7/2004 | Banerjee et al. |
| 2004/0193274 A1 | 9/2004 | Trieu |
| 2004/0228853 A1 | 11/2004 | Serhan et al. |
| 2004/0229786 A1 | 11/2004 | Attawia et al. |
| 2004/0229878 A1 | 11/2004 | DiMauro et al. |
| 2005/0025765 A1 | 2/2005 | DiMauro et al. |
| 2005/0038001 A1 | 2/2005 | Attawia et al. |
| 2005/0054595 A1 | 3/2005 | Binette et al. |
| 2005/0080113 A1 | 4/2005 | Ohkawa et al. |
| 2005/0090501 A1 | 4/2005 | Collis et al. |
| 2005/0100538 A1 | 5/2005 | Mohamed et al. |
| 2005/0112091 A1 | 5/2005 | DiMauro et al. |
| 2005/0208095 A1 | 9/2005 | Hunter et al. |
| 2005/0282783 A1 | 12/2005 | Bujoli et al. |
| 2006/0193920 A1 | 8/2006 | Bosch et al. |
| 2006/0210552 A1 | 9/2006 | Demopulos et al. |
| 2007/0237777 A1 | 10/2007 | DiMauro et al. |
| 2007/0243228 A1 | 10/2007 | McKay |
| 2007/0269413 A1 | 11/2007 | Serhan et al. |
| 2008/0213261 A1 | 9/2008 | DiMauro et al. |
| 2009/0068270 A1 | 3/2009 | Attawia et al. |
| 2009/0155364 A1 | 6/2009 | Serhan et al. |
| 2009/0162351 A1 | 6/2009 | Brown et al. |
| 2009/0162376 A1 | 6/2009 | Brown et al. |
| 2009/0175943 A1 | 7/2009 | Attawia et al. |
| 2009/0324558 A1 | 12/2009 | Attawia et al. |

FOREIGN PATENT DOCUMENTS

| | | |
|---|---|---|
| EP | 0 218868 A2 | 4/1987 |
| EP | 0 288 088 B1 | 10/1988 |
| EP | 0 438234 A1 | 7/1991 |
| EP | 0 950417 A2 | 2/1999 |
| EP | 1 133995 A2 | 9/2001 |
| EP | 1 153607 A2 | 11/2001 |
| EP | 1 464 307 A1 | 10/2004 |
| WO | WO 91/02078 A1 | 2/1991 |
| WO | WO 92/07076 A1 | 4/1992 |
| WO | WO 92/16553 A1 | 10/1992 |
| WO | WO 93/16099 A2 | 8/1993 |
| WO | WO 97/28828 A1 | 8/1997 |
| WO | WO 98/24477 A1 | 6/1998 |
| WO | WO 99/45923 A1 | 9/1999 |
| WO | WO 00/18409 | 4/2000 |
| WO | WO 00/50079 | 8/2000 |
| WO | WO 01/85179 A2 | 11/2001 |
| WO | WO 02/057240 A1 | 7/2002 |
| WO | WO 02/100387 A1 | 12/2002 |
| WO | WO 03/000190 A2 | 1/2003 |
| WO | WO 2004/022078 A1 | 3/2004 |
| WO | WO 2004/039248 | 5/2004 |
| WO | WO 2005/000283 A2 | 1/2005 |
| WO | WO 2005/011689 | 2/2005 |
| WO | WO 2005/049055 A1 | 6/2005 |
| WO | WO 2005/053795 | 6/2005 |
| WO | WO 2005/110276 A1 | 11/2005 |
| WO | WO 2006/031376 A2 | 3/2006 |

OTHER PUBLICATIONS

Abstracts of the N. American Spine Society 17 Annual Meeting, Montreal, Canada, Oct. 29 through Nov. 2, 2002, *The Spine Journal*, 2(5Suppl.). 49S-50S (2002).

Allai, F., et al., "Increase in Bone Mineral Density of Patients with Spondyloarthropathy Treated With Anti-Tumor Necrosis Factor α," *Ann. Rheum. Dis.*, 62:347-349 (2003).

Andonopoulos, A.P., et al., "Intra-articular Anti-Tumor Necrosis Factor α Antibody in Recalcitrant Arthritis of Behçet's Disease," *Clinical and Experimental Rheumatology 21*(4 Suppl 30): S-57-S58 (Jul.-Aug. 2003).

Aoki, Y., et al., "Local Application of Disc-Related Cytokines on Spinal Nerve Roots," *Spine*, 27(15): 1614-1617 (2002).

Ariga, K., et al., "Mechanical Stress-Induced Apoptosis of Endplate Chondrocytes in Organ-Cultured Mouse Intervertebral Discs," *Spine*, 28(14): 1528-1533 (2003).

Ashkenazi, A., et al., "Protection Against Endotoxic Shock by a Tumor Necrosis Factor Receptor Immunoadhesin," Proc. Natl. Acad. Sci. USA, 88, pp. 10535-10539.

Baker, D., et al., "Control Established Experimental Allergic Encephalomyelitis by Inhibition of Tumor Necrosis Factor (TNF) Activity Within the Central Nervous System using Monoclonal Antibodies and TNF Receptor-Immunoglobulin Fusion Proteins," *Eur. J. Immunol.*, 24:2040-2048 (1994).

Biskobing, D. M., "Novel Therapies for Osteoporosis," *Expert Opinion Invest. Drugs*, 12(4): 611-621 (2003).

Bokarewa, M., et al., "Local Infusion of Infliximab for the Treatment of Acute Joint Inflammation," *Ann. Rheum. Dis.*, downloaded from ard.bmjjournals.com on Nov. 30, 2005, www.annrheumdis.com 62:783-784 (2003).

Boehm, et al., "New Inhibitors of p38 Kinase," *Exp. Opin, Ther. Patents*, 10(1):25-37 (2000).

Braun, J. and Sieper J., "Overview of the Use of the Anti-TNF Agent Infliximab in Chronic Inflammatory Diseases," *Expert Opin. Biol. Ther.* 3(1):141-168 (2003).

Braun, J., et al., "Anti-Tumour Necrosis Factor α Therapy for Ankylosing Spondylitis: International Experience," *Ann. Rheum. Dis.*, 61(Supp. III):iii51-iii60 (2002).

Bringman, T.S. et al., "Monoclonal Antibodies to Human Tumor Necrosis Factors Alpha and Beta: Application for Affinity Purification, Immunoassays, and as Structural Probes," *Hybridoma*, 6(5):489-507 (1987).

Brown, K., et al., "Gelatin/Chondroitin 6-Sulfate Microspheres for the Delivery of Therapeutic Proteins to the Joint," *Arthritis. & Rheum.*, 41(12):2185-2195 (1998).

Burke, J.G., et al., "Intervertebral Discs Which Cause Low Back Pain Secrete High Levels of Proinflammatory Mediators," *J. Bone Joint Surg.* [Br] 84-B, 196-201 (2001).

Butler, D. et al., "TNF Receptor Fusion Proteins are Effective Inhibitors of TNF-Mediated Cytotoxicity on Human KYM-1D4 Rhabdomyosarcoma Cells," *Cytokine*, 6(6):616-623 (1994).

Capon, D. et al. "Designing CD4 Immunoadhesins for AIDS Therapy," Nature, 337:525-531 (1989).

Cardone, D. A., et al., "Diagnostic and Therapeutic Injection of the Hip and Knee," *Am. Fam. Physician*, 67(10): 2147-2152 (2003).

Chae, H.J. et al., "The p38 Mitogen-Activated Protein Kinase Pathway Regulates Interleukin-6 Synthesis in Response to Tumor Necrosis Factor in Osteoblasts," *Bone*, 28(1): 45-53 (2001).

Cirillo et al., "The Non-Diaryl Heterocycle Classes of p38 MAP Kinase Inhibitors," Current Topics in Medicinal Chemistry, 2: 1021-1035 (2002).

Conti, F., et al., "Successful Treatment With Intraarticular Infliximab for Resistant Knee Monarthritis in a Patient With Spondylarthropathy," *Arthritis & Rheumatism*, 52(4): 1224-1226 (2005).

Corcoran, A.E. et al., "Characterization of Ligand Binding by the Human p55 Tumour-Necrosis-Factor Receptor," *Eur. J. Biochem.*, 223:831-840 (1994).

Crandall, C., "Combination Treatment of Osteoporosis: A Clinical Review," *J. of Women's Health & Gender-Based Medicine*, 11(3):211-224 (2002).

Dayer, J.M., "The Pivotal Role of Interleukin-1 in the Clinical Manifestations of Rheumatoid Arthritis," *Rheumatology*, Oxford Univeristy Press, London, GB, 42(Suppl 2):ii03-ii10 (2003).

DeSantis, A. and Buchman, A., "Current and Emerging Therapies in Osteoporosis," *Expert Opin. Pharmacother.*, 3(7):835-843 (2002).

Diwan, A. D., et al., "Current Concepts in Intervertebral Disk Restoration," *Tissue Engineering in Orthopedic Surgery*, 31(3):453-464 (2000).

Engelmann, H. et al., "Two Tumor Necrosis Factor-Binding Proteins Purified From Human Urine," *J. Biol. Chem.*, 265(3):1531-1536 (1990).

Ezra, A., and Golomb, G., "Administration Routes and Delivery Systems of Bisphosphonates for the Treatment of Bone Resorption," *Adv. Drug Del. Rev.*, 42:175-195 (2000).

Fendly et al., "Murine Monoclonal Antibodies Defining Neutralizing Epitopes on Tumor Necrosis Factor," *Hybridoma*, 6:359-370 (1987).

Gabay, C., "IL-1 Trap," *Curr. Opin. Invest. Drugs, Curr. Drugs*, London, GB, 4(5):593-597 (2003).

Goodman, S. et al., "Effects of Local Infusion of TGFβ on Bone Ingrowth in Rabbit Chambers," *J. Biomed. Mat. Res. (Appl Biomater)*, 53:475-479 (2000).

Gordon, J. L., et al., "Metalloproteinase Inhibitors as Therapeutics," *Clin. Exp. Rheumatol.*, 11(Suppl. 8): S91-S94 (1993).

Goupille, P., et al., "Matrix Metalloproteinases the Clue to Intervertebral Disc Degeneration?," *Spine*, 23(14): 1612-1626 (1998).

Hirai, M. et al., "Production and Characterization of Monoclonal Antibodies to Human Tumor Necrosis Factor," *J. Immunol. Meth.*, 96:57-62 (1987).

Hunter, C. J., et al., "Functional Behaviour of Notochordal Cell Clusters in the Canine Nucleus Pulposus: Cell Communication and Survival," *70, Abstracts of the 30th Annual Meeting of the International Society for the Study of the Lumbar Spine*, Vancouver, Canada (May 2003).

Hydrogels, *Encyclopedia of Polymer Science and Technology*, (Wiley and Sons, 2003).

Johnson, W.H., et al., "Collagenase Inhibitors: Their Design and Potential Therapeutic Use," *J. Enzyme Inhib.*, 2:1-22 (1987).

Karppinen, J., et al., "Tumor Necrosis Factor—α Monoclonal Antibody, Infliximab, Used to Manage Severe Sciatica," *Spine*, 28(8):750-754 (2003).

Kawakami, M., et al., "Possible Mechanism of Painful Radiculopathy in Lumbar Disc Herniation," *Clin. Orthop.* 351:241-251(1998).

Kimble, R.B. et al., "Estrogen Deficiency Increases the Ability of Stromal Cells to Support Murine Osteoclastogenesis Via an InterLeukin-1 and Tumor Necrosis Factor-Mediated Stimulation of Macrophage Colony-Stimulating Factor Production," *J. Biol. Chem.* 271(46):28890-28897 (1996).

Kimble, R.B. et al., "The Functional Block of TNF but Not of IL-6 Prevents Bone Loss in Ovariectomized Mice," *J. Bone Min. Res.*, 12(6):935-941 (1997).

Koch, H. et al., "Spontaneous Secretion of Interleukin 1 Receptor Antagonist (IL-1Ra) by Cells Isolated From Herniated Lumbar Discal Tissue After Discectomy," *Cytokine*, 10(9): 703-705 (1998).

Kolls, J. et al. "Prolonged and Effective Blockade of Tumor Necrosis Factor Activity Through Adenovirus-Mediated Gene Transfer," *Proc. Natl. Acad. Sci. USA*, 91:215-219 (1994).

LaVan, D. A., et al., "Small-Scale Systems for in vivo Drug Delivery," *Nature, Biotechnology*, 21(10):1184-1191 (2003).

Lee, et al., "Inhibition of p38 MAP Kinase as a Therapeutic Strategy," *Immunopharmacology*, 47: 185-201 (2000).

Lehman, T. J. A., et al., "Thalidomide Therapy for Recalcitrant Systemic Onset Juvenile Rheumatoid Arthritis," *J. Pediatrics*, 140(1):125-127 (2002).

Lesslauer, W., et al., "Recombinant Soluble Tumor Necrosis Factor Receptor Proteins Protect Mice from Lipopolysaccharide-Induced Lethality," *Eur. J. Immunol.*, 21:2883-2886 (1991).

Liang, C.-M., et al., "Production and Characterization of Monoclonal Antibodies Against Recombinant Human Tumor Necrosis Factor/Cachectin," *Biochem. Biophys. Res. Comm.* 137(2):847-854 (1986).

Loetscher, H. et al., "Molecular Cloning and Expression of the Human 55 kd Tumor Necrosis Factor Receptor," *Cell*, 61:351-359 (1990).

Maeda, S. and Kokubun, S., "Changes With Age in Proteoglycan Synthesis in Cells Cultured In Vitro From the Inner and Outer Rabbit Annulus Fibrosus," *Spine*, 25(2):166-169 (2000).

Meager, A. et al., "Preparation and Characterization of Monoclonal Antibodies Directed Against Antigenic Determinants of Recombinant Human Tumour Necrosis Factor (rTNF)," *Hybridoma*, 6(3):305-311 (1987).

Möller, A. et al., "Monoclonal Antibodies to Human Tumor Necrosis Factor α: In Vitro and In Vivo Application," *Cytokine* 2(3):162-169 (1990).

Molloy, T., et al., "The Roles of Growth Factors in Tendon and Ligament Healing," *Sports Med.*, 33(5): pp. 381-394 (2003).

Müller, R. "Determination of Affinity and Specificity of Anti-Hapten Antibodies by Competitive Radioimmunoassay," *Meth. Enzymol.*, 92:589-601 (1983).

Nakamura, K. et al., "Local Application of Basic Fibroblast Growth Factor into the Bone Increases Bone Mass at the Applied Site in Rabbits," *Arch. Orthop. Trauma Surg.*, 115(6):344-346 (1996).

Nakamura, K. et al., "Stimulation of Endosteal Bone Formation by Local Intraosseous Application of Basic Fibroblast Growth Factor in Rats," *Rev. Rhum. [Engl. Ed.]*, 64(2):101-105 (1997).

Nikas, S. N., et al., "Treatment of Resistant Rheumatoid Arthritis by Intra-Articular Infliximab Injections: A Pilot Study," *Ann. Rheum. Dis.*, downloaded from ard.bmjjournals.com on Nov. 2, 2005, www.annrheumdis.com 63: 102-103 (2004).

Olmarker, K. and Rydevik, B., "Selective Inhibition of Tumor Necrosis Factor-α Prevents Nucleus Pulposus-Induced Thrombus Formation, Intraneural Edema, and Reduction of Nerve Conduction Velocity," *Spine*, 26(8): 863-869 (2001).

Pacifici, R., "Editorial: Cytokines, Estrogen, and Postmenopausal Osteoporosis—The Second Decade," *Endocrinology*, 139(6):2659-2661 (1998).

Pargellis, C. et al., "Inhibition of p38 MAP Kinase by Utilizing a Novel Allosteric Binding Site," *Nature Structural Biology*, 9(4): 268-272 (2002).

Pederson, A.W. et al., "Thermal Assembly of a Biomimetic Mineral/Collagen Composite," *Biomaterials*, 24:4881-4890 (2003).

Peppel, K. et al. "A Tumor Necrosis Factor (TNF) Receptor-IgG Heavy Chain Chimeric Protein as a Bivalent Antagonist of TNF Activity," *J. Exp. Med.*, 174:1483-1489 (1991).

Rodan, G.A. et al., "Therapeutic Approaches to Bone Diseases," *Science*, 289:1508-1514 (2000).

Schall, T. et al., "Molecular Cloning and Expression of a Receptor for Human Tumor Necrosis Factor," *Cell*, 61:361-370 (1990).

Schatteman, L., et al., "Treatment of Refractory Inflammatory Monoarthritis in Ankylosing Spondylitis by Intraarticular Injection of Infliximab," *J. Of Rheum.*, 33:1, pp. 82-85 (2006).

Stern, S., et al., "Human Intervertebral Disc Cell Culture for Disc Disorders," *Clin. Orthop.*, 419:238-244 (2004).

Takegami, K., et al., "Osteogenic Protein-1 Enhances Matrix Replenishment by Intervertebral Disc Cells Previously Exposed to Interleukin-1," *Spine*, 27(12):1318-1325 (2002).

Tobinick, E.L. and Davoodifar, S., "Perispinal TNF-alpha Inhibition for Discogenic Pain," *Swiss Med. Weekly*, 133:170-177 (2003).

Tobinick, E.L., "Targeted Etanercept for Discogenic Neck Pain: Uncontrolled, Open-Label Results in Two Adults," *Clin. Ther.*, 25(4):1211-1218 (2003).

Wittenberg, R.H., et al., "In Vitro Release of Prostaglandins and Leukotrienes From Synovial Tissue, Cartilage, and Bone in Degenerative Joint Diseases," *Arthritis Rheum.*, 36(10):1444-1450 (1993).

Yabuki, S., et al., "Prevention of Compartment Syndrome in Dorsal Root Ganglia Caused by Exposure to Nucleus Pulposus," *Spine*, 26(8):870-875 (2001).

Zhang, C., et al., "Mitogen-activated Protein (MAP) Kinase Regulates Production of Tumor Necrosis Factor-α and Release of Arachidonic Acid in Mast Cells," *J. Biol. Chem.*, 272(20): 13397-13402 (1997).

http://arthritis.com/od/kneetreatments/g/viscosupplement_p.htm, Dec. 9, 2005.

Kozbor, D. and Roder, J.C., "The Production of Monoclonal Antibodies from Human Lymphocytes," *Immunology Today*, 4(3):72-79 (1983).

Lane, N.E., et al., "Basic Fibroblast Growth Factor Forms New Trabeculae That Physically Connect with Pre-Existing Trabeculae, and this New Bone is Maintained With an Anti-Resorptive Agent and Enhanced With an Anabolic Agent in an Osteopenic Rat Model," *Osteoporos Int*, 14: 374-382 (2003).

Tobinick, E.L., "Targeted Etanercept for Treatment-Refractory Pain Due to Bone Metastasis: Two Case Reports," *Clinical Therapeutics*, 25(8):2279-2288 (2003).

Vahle, J.L., et al., "Skeletal Changes in Rats Given Daily Subcutaneous Injections of Recombinant Human Parathyroid Hormone (1-34) for 2 Years and Relevance to Human Safety," *Toxicologic Pathology*, 30(3):312-321 (2002).

Yaffe, A., et al., "Combined Local Application of Tetracycline and Bisphosphonate Reduces Alveolar Bone Resorption in Rats," *J Periodontol*, 74(7):1038-1042 (2003).

Alini, M., et al., "A Biological Approach to Treating Disc Degeneration: Not for Today, but Maybe for Tomorrow," *Eur. Spine J.*, 11 (Suppl. 2): S215-S220 (2002).

Connolly, J., et al., "Development of an Osteogenic Bone-Marrow Preparation," *The Journal of Bone and Joint Surgery, Inc.*, 71-A (5): 684-691 (1989).

Ganey, T. M. and Meisel, H. J., "A Potential Role for Cell-Based Therapeutics in the Treatment of Intervertebral Disc Herniation," *Eur. Spine J.*, 11 (Suppl. 2): S206-S214 (2002).

Sakai, D., et al., "Transplantation of Mesenchymal Stem Cells Embedded in Atelocollagen® Gel to the Intervertebral Disc: A Potential Therapeutic Model for Disc Degeneration," *Biomaterials*, 24: 3531-3541 (2003).

Ohtori, S., et al., "TNF-α and TNF-α Receptor 1 Upregulation in GLIA and Neurons After Nerve Injury. Studies in Murine DRG and Spinal Cord," 13, *Abstracts of the 30$^{th}$ Annual Meeting of the International Society for the Study of the Lumbar Spine*, Vancouver, Canada (May 2003).

Korhonen, T., et al., "Efficacy of Infliximab for Disc Herniation-Induced Sciatica One-Year Follow-Up," 14, *Abstracts of the 30$^{th}$ Annual Meeting of the International Society for the Study of the Lumbar Spine*, Vancouver, Canada (May 2003).

Sakai, D., et al., "Autologous Transplantation of Mesenchymal Stem Cells for Disc Repair," 24, *Abstracts of the 30$^{th}$ Annual Meeting of the International Society for the Study of the Lumbar Spine*, Vancouver, Canada (May 2003).

Le Visage, C., et al., "Interaction of Human Mescenchymal Stem Cells with Disc Cells: Changes in Biosynthesis of Extracellular Matrix," 25, *Abstracts of the 30$^{th}$ Annual Meeting of the International Society for the Study of the Lumbar Spine*, Vancouver, Canada (May 2003).

Risbud, M. V., et al., "Mesenchymal Stem Cells Respond to Their Microenvironment In Vitro to Assume Nucleus Pulposus-Like Phenotype," 26, *Abstracts of the 30$^{th}$ Annual Meeting of the International Society for the Study of the Lumbar Spine*, Vancouver, Canada (May 2003).

Richardson, S., et al., "Human Bone Marrow Mesenchymal Stromal Cells as a Source of Chondrocytes for Treatment of Intervertebral Disc Degeneration," 27, *Abstracts of the 30$^{th}$ Annual Meeting of the International Society for the Study of the Lumbar Spine*, Vancouver, Canada (May 2003).

Ahn, N. U., et al., "Effect of Nutrient Concentration and OP-1 on the Metabolism of Intervertebral Disc: In Vitro Organ Culture Study," 28, *Abstracts of the 30$^{th}$ Annual Meeting of the International Society for the Study of the Lumbar Spine*, Vancouver, Canada (May 2003).

Kwon, U-H., et al., "Dexamethsone Stimulates Cellular Proliferation While Downregulates Matrix Synthesis in Intervertebral Disc Cells," 29, *Abstracts of the 30$^{th}$ Annual Meeting of the International Society for the Study of the Lumbar Spine*, Vancouver, Canada (May 2003).

Li, J., et al., "The Effects of Bone Morphogenetic Protein 2 (BMP-2) and Cartilage-Derived Morphogentic Protein 2 (CDMP-2) on Aggrecan Gene Expression in Chondrocytes," 30, *Abstracts of the 30$^{th}$ Annual Meeting of the International Society for the Study of the Lumbar Spine*, Vancouver, Canada (May 2003).

Yoon, S. T., et al., "LMP-1 Upregulates Proteoglycan Synthesis in Intervertebral Disc Cells Through a BMP Mediated Process," 31, *Abstracts of the 30$^{th}$ Annual Meeting of the International Society for the Study of the Lumbar Spine*, Vancouver, Canada (May 2003).

Cornefjord, M., et al., "Cerebrospinal Fluid Biomarkers in Experimental Spinal Nerve Root Injury," 38, *Abstracts of the 30$^{th}$ Annual Meeting of the International Society for the Study of the Lumbar Spine*, Vancouver, Canada (May 2003).

Takada, T., et al., "IL-6 Production was Upregulated by Interaction Between Disc Tissue and Macrophages," 41, *Abstracts of the 30$^{th}$ Annual Meeting of the International Society for the Study of the Lumbar Spine*, Vancouver, Canada (May 2003).

Inui, Y., et al., "Fas-Ligand Expression on Nucleus Pulposus Cells Begins in Developing Embryo," 42, *Abstracts of the 30$^{th}$ Annual Meeting of the International Society for the Study of the Lumbar Spine*, Vancouver, Canada (May 2003).

Sobajima, S., et al., "Stem Cell Therapy for Degenerative Disc Disease: An In-Vitro Feasibility Study," 43, *Abstracts of the 30$^{th}$ Annual Meeting of the International Society for the Study of the Lumbar Spine*, Vancouver, Canada (May 2003).

Imai, Y., et al., "The Quantification of Cytokine-Induced Matrix Catabolism in Tissue Engeneered Intervertebral Discs," 67, *Abstracts of the 30$^{th}$ Annual Meeting of the International Society for the Study of the Lumbar Spine*, Vancouver, Canada (May 2003).

Hunter, C. J., et al., "Functional Behavior of Notochordal Cell Clusters in the Canine Nucleus Pulposus: Cell Communication and Survival," 70, *Abstracts of the 30$^{th}$ Annual Meeting of the International Society for the Study of the Lumbar Spine*, Vancouver, Canada (May 2003).

Tsuji, T., et al., "Age-Related Changes in M-RNA Expression of Various Regulatory Factors in Rabbit Intervertebral Disc," 81, *Abstracts of the 30$^{th}$ Annual Meeting of the International Society for the Study of the Lumbar Spine*, Vancouver, Canada (May 2003).

Miyamoto, H., et al., "The Effect of Mechanical Stress on the Production of Inflammatory Agents by Disc Cells," 110, *Abstracts of the 30$^{th}$ Annual Meeting of the International Society for the Study of the Lumbar Spine*, Vancouver, Canada (May 2003).

Arai, I., et al., "Pretreatment with Loxoprofen Sodium, 6-OHDA or Anti TNF-Alpha Antibody Reduce Fos-Like Immunoreactivity in Rat Experimental Lumber Disc Herniation," 111, *Abstracts of the 30$^{th}$ Annual Meeting of the International Society for the Study of the Lumbar Spine*, Vancouver, Canada (May 2003).

Edwards, S. L., et al., "Radiographic Assessment of Posterolateral Spine Fusion With and Without Platelet Rich Plasma," 117, *Abstracts of the 30$^{th}$ Annual Meeting of the International Society for the Study of the Lumbar Spine*, Vancouver, Canada (May 2003).

Xie, X., et al., "Treatment of Spondylodiscitis Intravenous Versus Percutaneous Intradiscal Applications of Antibiotics: An Experimental Study in Rabbits," 120, *Abstracts of the 30$^{th}$ Annual Meeting of the International Society for the Study of the Lumbar Spine*, Vancouver, Canada (May 2003).

Frain, J., et al., "Use of cDNA Microarrays to Investigate Cytokine Expression in Intervertebral Disc Degeneration," 126, *Abstracts of the 30$^{th}$ Annual Meeting of the International Society for the Study of the Lumbar Spine*, Vancouver, Canada (May 2003).

Hashizume, H., et al., "Role of IL-8, MCP-1 and PH in Neuropathic Pain Enhanced by Degenerative Nucleus Pulposus," 127, *Abstracts of the 30$^{th}$ Annual Meeting of the International Society for the Study of the Lumbar Spine*, Vancouver, Canada (May 2003).

Lotz, J. C., et al., "Cytokines in Normal, Degenerated, and Nucleoplasty-Treated Porcine Discs," 157, *Abstracts of the 30$^{th}$ Annual Meeting of the International Society for the Study of the Lumbar Spine*, Vancouver, Canada (May 2003).

Okuma, M., et al., "Rotary Cell Culture System Stimulates Annulus Fibrosus Cell Proliferation but Suppresses Proteoglycan Metabolism," 164, *Abstracts of the 30$^{th}$ Annual Meeting of the International Society for the Study of the Lumbar Spine*, Vancouver, Canada (May 2003).

Burke, J. G., et al., "Human Nucleus Pulposus Secretes Transforming Growth Factor Beta-1 and Basic Fibroblast Growth Factor," 189, *Abstracts of the 30$^{th}$ Annual Meeting of the International Society for the Study of the Lumbar Spine*, Vancouver, Canada (May 2003).

Kato, H., et al., "The Effect of IL-1 on the Rabbit Intervertebral Disc In Vivo," 199, *Abstracts of the 30$^{th}$ Annual Meeting of the International Society for the Study of the Lumbar Spine*, Vancouver, Canada (May 2003).

Imai, Y., et al., "Effect of Recombinant Human Osteogenic Protein-1 on Extracellular Matrix Metabolism by Human Annulus Fibrosus and Nucleus Pulposus Cells," 205, *Abstracts of the 30th Annual Meeting of the International Society for the Study of the Lumbar Spine*, Vancouver, Canada (May 2003).

Lee, C. S., et al., "A Single Period of Hyperphysiologic Stretch Induces IL-6, TGF-beta and Cell Proliferation in Anulus Fibrosus Cells," 215, *Abstracts of the 30th Annual Meeting of the International Society for the Study of the Lumbar Spine*, Vancouver, Canada (May 2003).

Le Maitre, C. L., et al., "Response of Human Intervertebral Disc Cells to IL-1," 216, *Abstracts of the 30th Annual Meeting of the International Society for the Study of the Lumbar Spine*, Vancouver, Canada (May 2003).

Le Maitre, C. L., et al., "Expression of the IL-1 Family in Human Intervertebral Disc," 217, *Abstracts of the 30th Annual Meeting of the International Society for the Study of the Lumbar Spine*, Vancouver, Canada (May 2003).

Weiler, C., et al., "Expression of TNF-α in Autopsy and Biopsy Specimens of Intervertebral Discs of Various Age and Degeneration," 233, *Abstracts of the 30th Annual Meeting of the International Society for the Study of the Lumbar Spine*, Vancouver, Canada (May 2003).

Ohtori, S., et al., "TNF-α-Deficient Mice Have Fewer Macrophages in Injured Nerve and Reduced Glial Activation in DRG and Spinal Cord," 250, *Abstracts of the 30th Annual Meeting of the International Society for the Study of the Lumbar Spine*Vancouver, Canada (May 2003).

Igarashi, A., et al., "Inflammatory Cytokines Release From Facet Joint Tissue in Degenerative Lumbar Disorders," 262, *Abstracts of the 30th Annual Meeting of the International Society for the Study of the Lumbar Spine*, Vancouver, Canada (May 2003).

Abbas-Ghaleb, K. et al, "Preconcentration of Selenium Compounds on a Porous Graphitic Carbon Column in View of HPLC-ICP-AES Speciation Analysis," *Anal. Bioanal. Chem.*, 377:1026-1031 (2003).

Awasthi, Y.C. et al., "Purification and Properties of Human Erythrocyte Glutathione Peroxidase," *J. Biol. Chem.*, 250(13):5144-5149 (1975).

Biemond, P. et al., "Protective Factors Against Oxygen Free Radicals and Hydrogen Peroxide in Rheumatoid Arthritis Synovial Fluid," *Arthritis Rheum.*, 27(7):760-765 (1984).

Ceponis, A. et al. "Effects of Low-Dose, Noncytotoxic, Intraarticular Liposomal Clodronate on Development of Erosions and Proteoglycan Loss in Established Antigen-Induced Arthritis in Rabbits," *Arthritis and Rheum.*, 44(8): 1908-1916 (2001).

Chan, J.M.K. et al., "Intraarticular Gene Transfer of TNFR:Fc Suppresses Experimental Arthritis with Reduced Systemic Distribution of the Gene Product," *Mol. Ther.*, 6(6): 727-736 (2002).

Desai, S. et al., "Coated Microwell Plate-Based Affinity Purification of Antigens," *Anal. Biochem.*, 328: 162-165 (2004).

Guillen, C. et al., "The Effects of Local Administration of Lactoferrin on Inflammation in Murine Autoimmune and Infectious Arthritis," *Arthritis Rheum.*, 43(9):2073-2080 (2000).

Hayashida, K. et al., "Lactoferrin Enhances Peripheral Opioid-Mediated Antinociception via Nitric Oxide in Rats," *Eur. J. Pharmacol.*, 484:175-181 (2004).

Hayashida, K. et al., "Oral Administration of Lactoferrin Inhibits Inflammation and Nociception in Rat Adjuvant-Induced Arthritis," *J. Vet. Med. Sci.*, 66(2):149-154(2004).

Kamanh, A. et al., "Plasma Lipid Peroxidation and Antioxidant Levels in Patients with Rheumatoid Arthritis," *Cell Biochem. Funct.*, 22:53-57 (2004).

Kilic, B.A. et al., "Effects of Intra-Articular Vitamin E and Corticosteroid Injection in Experimental Hemarthrosis in Rabbits," *Pediatr. Hematol. Oncol.*, 15(4):339-346 (1998).

Kim, S.H. et al. "Ex Vivo Gene Delivery of IL-1Ra and Soluble TNF Receptor Confers a Distal Synergistic Therapeutic Effect in Antigen-Induced Arthritis," *Mol. Ther.*, 6(5): 591-600 (2002).

Kurz, B. et al., "Dietary Vitamins and Selenium Diminish the Development of Mechanically Induced Osteoarthritis and Increase the Expression of Antioxidative Enzymes in the Knee Joint of STR/1N Mice," *Osteoarthritis Cartilage*, 10:119-126 (2002).

Lubberts, E. et al., "Intra-Articular IL-10 Gene Transfer Regulates the Expression of Collagen-Induced Arthritis (CIA) in the Knee and Ipsilateral Paw," *Clin. Exp. Immunol.*, 120:375-383 (2000).

Maddipati, K.R. and Marnett, L.J., "Characterization of the Major Hydroperoxide-Reducing Activity of Human Plasma," *J. Biol. Chem.*, 262(36):17398-17403 (1987).

Martinez, J.I.R., et al, "Blood Platelet Glutathione Peroxidase: Some Properties and Partial Purification," *Thromb. Res.*, 19:73-83 (1980).

Niccoli, L. et al., "Intraarticular Injection of Infliximab in Relapsing Knee Effusion in Psoriatic Arthritis: A Pilot Study," *Ann. Rheum. Dis.*, 62(1); 239-240 (2003) and EULAR—Annual European Congress of Rheumatology, Lisbon, Portugal (2003) (abstract).

Nikas, S.N., et al., "Treatment of Resistant Rheumatoid Arthritis by Intra-Articular Injections with Infliximab: A Pilot Study," *Ann. Rheum. Dis.* 62(1): 408 (2003) and EULAR—Annual European Congress of Rheumatology, Lisbon, Portugal (2003) (abstract).

Salin, M.L. and McCord, J.M., "Free Radicals and Inflammation: Protection of Phagocytosing Leukocytes by Superoxide Dismutase," *J. Clin. Invest.*, 56:1319-1323 (1975).

Schalkwijk, J. et al., "Cationization of Catalase, Peroxidase, and Superoxide Dismutase," *J. Clin. Invest.*, 76:198-205 (1985).

Steer, J.H. et al., "Altered Leucocyte Trafficking and Suppressed Tumour Necrosis Factor α Release from Peripheral Blood Monocytes After Intra-Articular Glucocorticoid Treatment," *Ann. Rheum. Dis.*, 57(12): 732-737 (1998).

Stepanik, T.M. and Ewing, D.D., "Coisolation of Glutathione Peroxidase, Catalase and Superoxide Dismutase from Human Erythrocytes," *J. Biochem. Biophys. Methods*, 20:157-169 (1990).

Tiku, M.L. et al., "Aggrecan Degradation in Chondrocytes is Mediated by Reactive Oxygen Species and Protected by Antioxidants," *Free Radic. Res.*, 30:395-405 (1999).

Tiku, M.L. et al., "Evidence Linking Chondrocyte Lipid Peroxidation to Cartilage Matrix Protein Degradation," *J. Biol. Chem.*, 275(26):20069-20076 (2000).

Trif, M. et al., "Liposomes as Possible Carriers for Lactoferrin in the Local Treatment of Inflammatory Diseases," *Exp. Biol. Med.*, 226(6):559-564 (2001).

Williams, A.S. et al., "Amelioration of Rat Antigen-Induced Arthritis by Liposomally Conjugated Methotrexate is Accompanied by Down-Regulation of Cytokine mRNA Expression," *Rheumatology*, 40:375-383 (2001).

Yang, J.G. et al., "Purification and Quantitation of a Rat Plasma Selenoprotein Distinct from Glutathione Peroxidase Using Monoclonal Antibodies," *J. Biol. Chem.*, 262(27):13372-13375 (1987).

Ando, N., et al., "An Immunohistochemical Study of the Degenerative Lumbar Disc," Orthopedics & Traumatology 44(1): 176-178 (1995) (Published in Japanese with English Abstract).

Blight, A.R., "Miracles and molecules—progress in spinal cord repair," Nature Neuroscience Supplement 5:1051-1054 (Nov. 2002).

Castro, R., et al., "Failure of Bone Marrow Cells to Transdifferentiate Into Neural Cells in Vivo," Science, 297: 1299 (2002).

Gori, A., et al., "Tumor Necrosis Factor-α Increased Production During Thalidomide Treatment in Patients With Tuberculosis and Human Immunodeficiency Virus Coinfection," The Journal of Infectious Diseases, 182: 639 (2000).

Höke, A., "Mechanisms of Disease: what factors limit the success of peripheral nerve regeneration in humans?," Nature Clinical Practice Neurology, 2(8): 448-454 (Aug. 2006).

Kawakami, M., et al., "Role of IL-8, MCP-1 and PH in Neuropathic Pain Enhanced by Degenerative Nucleus Pulposus," 127, Abstracts of the 30th Annual Meeting of the International Society for the Study of the Lumbar Spine, Vancouver, Canada (May 2003).

Meijer, H., et al., "The Production of Anti-inflammatory Cytokines in Whole Blood by Physico-chemical Induction," Inflamm. Res., 52: 404-407 (2003).

Yorimitsu, E., "A Comparative Study on the Pathological Changes of Intervertebral Discs after Intradiscal Injection of Various Kinds of Steroid Materials: An Experimental Study," Journal Keio Medical Society 74(5): 303-315 (1997) (Published in Japanese with English Abstract).

Marriott, J.B. et al., "CC-3052: A Water-Soluble Analog of Thalidomide and Potent Inhibitor of Activation-Induced TNF-α Production," *J. Immunol.*, 161:4236-4243 (1998).

Ohno, K. and Oshita, S., "Transdiscal Lumbar Sympathetic Block: A New Technique for a Chemical Sympathectomy," *Anesth. Analg.*, 85:1312-1316 (1997).

Hawks, D., "Alternative Medicine: Musculoskeletal System," *Clin. Tech. Small Anim. Pract.*, 17(1):41-49 (2002).

Khot, A. et al., "The Use of Intradiscal Steroid Therapy for Lumbar Spinal Discogenic Pain—A Randomized Controlled Trial," *Spine*, 29(8):833-837 (2004).

Földes, I. et al., "Trace Elements in Tissues of Normal and Vitamin $D_2$-Treated Rats," *ACTA Biol. Acad. Sci. Hung.*, 26(3-4):141-150 (1975).

Benjamin, L.E. et al., "A Plasticity Window for Blood Vessel Remodelling is Defined by Pericyte Coverage of the Preformed Endothelial Network and is Regulated by PDGF-B and VEGF," *Development*, 125:1591-1598 (1998).

Vukicevic, S. et al., "Induction of Nephrogenic Mesenchyme by Osteogenic Protein 1 (Bone Morphogenetic Protein 7)," *Proc. Natl. Acad. Sci.*, 93:9021-9026 (1996).

Moreira, A.L. et al., "Thalidomide Exerts Its Inhibitory Action on Tumor Necrosis Factor α by Enhancing mRNA Degradation," *J. Exp. Med.*, 177:1675-1680 (1993).

CN 1 647 808 A (Zhou C) Aug. 3, 2005 (abstract) World Patents Index [online]. London, GB: Derwent Publications, Ltd., Week 200621, Accession No. 2006-194507.

CN 1 569 039 A (Niu X) Jan. 26, 2005 (abstract) World Patents Index [online]. London, GB: Derwent Publications, Ltd., Week 200577, Class B04, Accession No. 2005-749289.

Shiel, W.C., Ankylosing Spondylitis, MedicineNet.com [online], Sep. 2005 [retrieved on Jun. 20, 2006]. Retrieved from the Internet <URL: http://www.medicinenet.com/script/main/art.asp?articlekey=274&pf=3&page=2>.

Sampaio, E.P. et al, "Thalidomide Selectively Inhibits Tumor Necrosis Factor α Production by Stimulated Human Monocytes," *J. Exp. Med.*, 173:699-703 (1991).

Muller, G.W. et al., "Amino-Substituted Thalidomide Analogs: Potent Inhibitors of TNF-α Production," *Bioorg. Med. Chem. Lett.*, 9:1625-1630 (1999).

Teo, S.K., "Properties of Thalidomide and its Analogues: Implications for Anticancer Therapy," *AAPS Journal* 7(1):E14-E19 (2005).

Tracey, K.J. and Cerami, A., "Tumor Necrosis Factor in Metabolism of Disease: Hormonal Actions Versus Local Tissue Effects," *Nouv. Rev. Fr. Hematol.*, 34 Suppl:S37-42 (1992) (abstract).

Haro, H. et al., "Matrix Metalloproteinase-7-Dependent Release of Tumor Necrosis Factor-α in a Model of Herniated Disc Resorption," *J. Clin. Invest.*, 105(2):143-150 (2000).

Office Action, U.S. Appl. No. 11/881,926, dated Apr. 3, 2009.
Final Office Action, U.S. Appl. No. 11/881,926, dated Dec. 23, 2009.
Office Action (RR), U.S. Appl. No.10/456,948, mailed Feb. 14, 2006.
Office Action, U.S. Appl. No. 10/456,948, mailed Aug. 29, 2006.
Final Office Action, U.S. Appl. No. 10/456,948, mailed Mar. 30, 2007.
Notice of Allowance, U.S. Appl. No. 10/456,948, mailed Jun. 29, 2007.
Notice of Allowance after RCE filed, U.S. Appl. No. 10/456,948, mailed Oct. 18, 2007.

Bullington, J. et al., "Inhibitors of Unactivated p38 MAP Kinase," *Bioorg. Med. Chem. Let.*, 16, 6102-6106 (2006).

Dernis, E., et al., "Infliximab in spondylarthropathy—influence on bone density," *Clin. Exp. Rheumatol.*, 20 (6 Suppl 28): S185-6 (2002).

Office Action (RR), U.S. Appl. No. 10/610,355, mailed Jun. 16, 2006.
Office Action, U.S. Appl. No. 10/610,355, mailed Sep. 19, 2006.
Final Office Action, U.S. Appl. No. 10/610,355, mailed Mar. 27, 2007.
Office Action, U.S. Appl. No. 10/610,355, mailed Aug. 16, 2007.
Notice of Allowability, U.S. Appl. No. 10/610,355, mailed May 15, 2008.
Office Action (RR), U.S. Appl. No. 11/881,925, mailed Oct. 15, 2008.
Office Action, U.S. Appl. No. 11/881,925, mailed May 13, 2009.
Final Office Action, U.S. Appl. No. 11/881,925, mailed Dec. 30, 2009.
Office Action (RR), U.S. Appl. No. 10/631,487, mailed Oct. 6, 2006.
Office Action, U.S. Appl. No. 10/631,487, mailed Jan. 29, 2007.
Final Office Action, U.S. Appl. No. 10/631,487, mailed Jul. 26, 2007.
Office Action, U.S. Appl. No. 10/631,487, mailed Mar. 10, 2008.
Office Action, U.S. Appl. No. 10/631,487, mailed Nov. 13, 2008.
Office Action, U.S. Appl. No. 10/631,487, mailed Jul. 20, 2009.
Final Office Action, U.S. Appl. No. 10/631,487, mailed Apr. 12, 2010.
Office Action (RR), U.S. Appl. No. 12/005,060, mailed Nov. 13, 2009.
Office Action, U.S. Appl. No. 12/005,060, mailed Mar. 31, 2010.
Final Office Action, U.S. Appl. No. 12/005,060, mailed Dec. 7, 2010.
Office Action (RR), U.S. Appl. No. 12/291,378, mailed Jun. 24, 2010.
Office Action, U.S. Appl. No. 12/291,378, mailed Sep. 30, 2010.
Office Action (RR), U.S. Appl. No. 12/290,998, mailed Jun. 24, 2010.
Office Action, U.S. Appl. No. 12/290,998, mailed Sep. 30, 2010.
Final Office Action dated Apr. 18, 2011 for U.S. Appl. No. 12/291,378.
Office Action dated Apr. 19, 2011 for U.S. Appl. No. 12/290,998.

't Hart, B.A. and Amor, S., "The use of animal models to investigate the pathogenesis of neuroinflammatory disorders of the central nervous system," *Curr. Opin. Neurol.*, 16:375-383 (2003).

Bertolini, D.R., et al., "Stimulation of Bone Resorption and Inihibition of Bone Formation in vitro by Human Tumour Necrosis Factors," *Nature*, 319:516-518 (1986).

Brandt, J., et al., "Successful Treatment of Active Ankylosing Spondylitis With the Anti-Tumor Necrosis Factor α Monoclonal Antibody Infliximab," *Arthritis & Rheumatism*, 43(6):1346-1352 (Jun. 2000).

Schmidt, C.E. and Leach, J.B., "Neural Tissue Engineering: Strategies for Repair and Regeneration," *Annu. Rev. Biomed. Eng.* 5:293-347 (Jun. 2003).

Séguin, C.A., et al., "Tumor Necrosis Factor α Modulates Matrix Production and Catabolism in Nucleus Pulposus Tissue," *Spine* 30(17):1940-1948 (Sep. 1, 2005).

Kitazawa, R., et al., "Interleukin-1 Receptor Antagonist and Tumor Necrosis Factor Binding Protein Decrease Osteoclast Formation and Bone Resorption in Ovariectomized Mice," *J. Clin. Invest.*, 94:2397-2406 (1994).

Marzo-Ortega, H., et al., "Bone mineral density improvement in spondyloarthropathy after treatment with etanerecept," *Ann. Rheum. Dis.*, 62:1020-1021 (2003).

McIntyre, C.J., et al., "Pyridazine Based Inhibitors of p38 MAPK," *Bioorg. Med. Chem. Lett.*, 12:689-692 (2002).

Muthumani, K., et al., "Suppression of HIV-1 viral replication and cellular pathogenesis by a novel p38/JNK kinase inhibitor," *AIDS*, 18:730-748 (2004).

Rupert, K.C., et al., "Imidazopyrimidines, Potent Inhibitors of p38 MAP Kinase," *Bioorg. Med. Chem. Lett.*, 13:347-350 (2003).

Schaible, H-G, et al., "The Role of Proinflammatory Cytokines in the Generation and Maintenance of Joint Pain," *Ann. N.Y. Acad. Sci.*, 1193:60-69 (2010).

Office Action U.S. Appl. No. 12/291,016 dated Mar. 11, 2011.
Notice of Allowance U.S. Appl. No. 12/291,016 mailed Dec. 9, 2011.
Office Action U.S. Appl. No. 12/454,200 dated Aug. 25, 2010.
Final Office Action U.S. Appl. No. 12/454,200 dated Feb. 1, 2011.
Notice of Allowance U.S. Appl. No. 12/454,200 dated Apr. 7, 2011.
Notice of Allowance U.S. Appl. No. 12/454,200 dated Jul. 18, 2011.
Office Action U.S. Appl. No. 11/881,925, mailed Nov. 17, 2011.
International Preliminary Report on Patentability, PCT/US2004/037500 mailed May 15, 2006.
Written Opinion, PCT/US2004/037500 mailed May 15, 2006.
International Search Report, PCT/US2004/037500 mailed Mar. 24, 2005.

Hotten, et al., "Recombinant Human Growth/Differentiation Factor 5 Stimulates Mesenchyme Aggregation and Chondrogenesis Responsible for the Skeletal Development of Limbs," *Growth Factors*, 13: 65-74 (1996).

\* cited by examiner

AUTOLOGOUS TREATMENT OF DEGENERATED DISC WITH CELLS

RELATED APPLICATIONS

This application is a continuation-in-part application U.S. application Ser. No. 10/714,559, filed Nov. 13, 2003, now abandoned, which is a continuation-in-part of U.S. application Ser. No. 10/631,487, filed Jul. 31, 2003, which is a continuation-in-part application of U.S. application Ser. No. 10/610,355, filed Jun. 30, 2003, now U.S. Pat. No. 7,429,378 which is a continuation-in-part application of U.S. application Ser. No. 10/456,948, filed Jun. 6, 2003, now U.S. Pat. No. 7,344,716 which claims the benefit of priority from U.S. Provisional Application No. 60/470,098, filed May 13, 2003. The entire teachings of the above applications are incorporated herein by reference.

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, the cells within the nucleus pulposus form only about one percent of the disc tissue by volume. These cells produce an extracellular matrix (ECM) containing a high percentage of proteoglycans. These proteoglycans contain sulfated functional groups that retain water, thereby providing the nucleus pulposus with its cushioning qualities. The nucleus pulposus cells may also secrete small amounts of cytokines as well as matrix metalloproteinases (MMPs). These cytokines and MMPs help regulate the metabolism of the nucleus pulposus cells.

In some instances of disc degeneration disease (DDD), gradual degeneration of the intervertebral disc is caused by mechanical instabilities in other portions of the spine. In these instances, increased loads and pressures on the nucleus pulposus cause the cells within the disc (or invading macrophages) to emit larger than normal amounts of the above-mentioned cytokines. In other instances of DDD, genetic factors or apoptosis can also cause a decline in the number of disc cells and/or release of toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to provide nutrients to the cells and eliminate waste may result in decreased cell viability and metabolism resulting in further degradation of the ECM along with the accumulation of high levels of toxins that may cause nerve irritation and pain.

As DDD progresses, toxic levels of the cytokines and MMPs present in the nucleus pulposus begin to degrade the ECM. In particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, typically thereby upregulating MMPs. As this destructive cascade continues and DDD further progresses, the disc begins to bulge ("a herniated disc"), and then ultimately ruptures, causing the nucleus pulposus to contact the spinal cord and produce pain.

U.S. Pat. No. 6,352,557 ("Ferree") teaches adding therapeutic substances such as nucleus pulposus cells to morselized extra-cellular matrix obtained from donors, and injecting that combination into an intervertebral disc. However, the cells first need to be cultured and then added to the donor matrix prior to implantation into the diseased disc. This process requires a delay in the patient's treatment in addition to subjecting the patient to two separate procedures. The first procedure is to harvest the cells, which then require culturing. Following the culturing the cells are implanted into the patient.

U.S. Pat. No. 6,340,369 ("Ferree II") teaches harvesting live intervertebral disc cells from a patient, culturing the cells and transplanting them into the affected disc. Ferree II further teaches that the cells can be combined with Type II collagen-glycosaminoglycan matrix or Type I collagen-glycosaminoglycan matrix depending on whether the cells are harvested from the nucleus pulposus (NP) or annulus fibrosus (AF). Also Ferree II suggests adding one or more therapeutic substances to cells prior to transplantation. As an alternate source for cells, Ferree proposes using precursor cells of NP or AF cells, chondrocytes or other living cells that function like or could differentiate into NP or AF cells. Throughout, Ferree teaches that the harvested cells are cultured prior to transplantation.

Alini, Eur. Spine J., 11(Supp.2): S215-220 (2002), suggests that injection of a biomatrix embedded with cells will have the potential to restore functionality to the disc. Alini's experiments are directed to isolating cells from the nucleus pulposus and culturing them. Alini also suggests other sources of cells including disc cells from allogenic donors and autologous stem cells. His teachings suggest that stem cells would be an ideal source but that there are no known methods for culturing the stem cells such that they would differentiate into nucleus pulposus cells prior to implantation. In essence, Alini requires that cells be cultured prior to implantation.

Russell (Abstract 27 ISSLS 2003) reports conducting an experiment to determine whether mesenchymal stem cells (MSCs) could be directed to present disc chondrocyte phenotypes. Russell found that adult human MSCs were induced to differentiate along a chondrocytic phenotype when mediated by culture conditions and also by addition of TGF-B1.

Sakai (Abstract 24 ISSLS 2003) reports evaluating whether autologous transplantation of MSCs to the disc would prevent disc degeneration. Using rabbits, MSCs were isolated from the bone marrow and cultured for 2 weeks prior to transplantation. Results showed significant disc preservation.

Sakai, Biomaterials, 24: 3531-3541 (2003) describes using a final cell density of $1 \times 10^6$ cells/ml, to inject 0.04 ml of solution in which autogenous cultured MSCs were embedded through a 27-gauge insulin injector to each disc. Proliferation of cells after transplantation was found to be successful.

Sobajima (Abstract 43 ISSLS 2002) studied the feasibility of stem cell therapy for DDD. Human NP cells were isolated from patients undergoing disc surgery and were co-cultured with either MSCs from patients undergoing hip surgery or muscle derived stem cells from mice. The data demonstrated a synergistic effect between stem cells and nucleus pulposus cells, resulting in upregulated proteoglycan synthesis in vivo.

Ganey, Eur Spine J, 11 (Suppl.2):S206-S214 (2002), reported on surgeries conducted in Germany where cells were harvested from portions of a patient's disc after discectomy. The cells were then cultured and returned for transplantation into the patient at a later date.

Sander et al. in U.S. Patent Application Publication 2003/0069639, teaches using tissue biopsies taken from a patient as a source to harvest cells for implantation into a degenerated disc.

All of the teachings cited above require culturing of cells prior to implantation, which, in turn, necessitates a delay in treating the patient's degenerating disc.

SUMMARY OF THE INVENTION

The present inventors have developed an intra-operative procedure for efficaciously treating degenerative disc disease by introducing autologous uncultured cells, (e.g., mesenchymal stem cells or chondrocytes or fibroblasts) into the patient's disc. This procedure provides immediate point of care treatment for the patient.

In accordance with one embodiment of the present invention, the present inventors have developed a method of treating an intervertebral disc in which cells harvested from the patient's bone marrow are then introduced into the degenerated disc to differentiate into nucleus pulposus and/or annulus fibrosus cells present in the disc, thereby increasing the number of those cells present in the disc. In some embodiments, the implantation of the cells into the disc can occur immediately following the harvesting of the cells, so that the patient can avoid undergoing a first procedure to harvest the cells, waiting for the cells to be cultured (which may take several weeks), and then returning for a second procedure to implant the cultured cells into the disc.

There are believed to be several advantages to introducing cells to a targeted disc. A primary function of the cells is to produce extra-cellular matrix. As described above, there are several factors that result in cell death or malfunction, which in turn contribute to the degradation of this matrix. One strategy to rebuild or regenerate the extra-cellular matrix is to increase the number of viable functioning disc cells producing the matrix. The inventors' believe that the plasticity phenomenon of the mesenchymal stem cells (MSCs) makes them an ideal choice of cell type for differentiating into disc cells after implantation into the targeted disc. The cells may become nucleus pulposus (NP) and/or annulus fibrosus (AF) cells that will be capable of producing the necessary extra-cellular matrix within the disc. In addition, at the time of implantation, the cells may be combined with other therapeutic agents such as growth factors to help the cells survive, once inside the disc.

Accordingly, in one aspect of the present invention, there is provided a method of treating degenerative disc disease in an intervertebral disc, comprising harvesting MSCs from a patient, and introducing the viable MSCs, without having to culture them, into the same patient's degenerated intervertebral disc, where the cells will proliferate and differentiate into nucleus pulposus and/or annulus fibrosus cells.

In some embodiments, the cells are delivered alone or via a carrier. In other embodiments, the cells are delivered along with an additional therapeutic agent or substance such as a growth factor to the disc.

DETAILED DESCRIPTION OF THE INVENTION

Because DDD is a continuous process, the degenerating disc to which the cells are administered may be in any one of a number of degenerative states. Accordingly, the degenerating disc may be an intact disc. The degenerating disc may be a herniated disc (i.e., wherein a portion of the annulus fibrosus has a bulge). The degenerating disc may be a ruptured disc (i.e., wherein the annulus fibrosus has ruptured and the bulk nucleus pulposus has exuded). The degenerating disc may be delaminated (i.e., wherein adjacent layers of the annulus fibrosus have separated). The degenerating disc may have fissures (i.e., wherein the annulus fibrosus has fine cracks or tears through which selected molecules from the nucleus pulposus can leak). In all of these degenerative states, the extra-cellular matrix of either the AF or NP is also degrading.

The present invention is directed to intra-operatively providing healthy, viable autologous mesenchymal stem cells (MSCs) to a degenerated intervertebral disc of a patient. The cells may be delivered to either the nucleus pulposus or the annulus fibrosus or both for repair and restoration of each respective extra-cellular matrix.

The inventors believe that MSCs provide a special advantage for administration into a degenerating disc because they possess properties that will help them to more readily survive the relatively harsh environment present in the degenerating disc. Specifically, MSCs have a desirable level of plasticity that gives them the ability to proliferate and differentiate into NP and AF cells.

In one embodiment, the MSCs are obtained from the patient's own bone marrow. In other embodiments, adipose or muscle tissue may be the source of MSCs. In some embodiments, the MSCs to be administered to the disc are provided in a concentrated form. When provided in concentrated form, the cells can be uncultured. Uncultured, concentrated MSCs can be readily obtained by centrifugation, filtration (selective retention), or immunoabsorption. When filtration is selected, the methods disclosed in U.S. Pat. No. 6,049,026 ("Muschler"), the contents of which are incorporated by reference in their entirety, can be used. In some embodiments, the matrix used to filter and concentrate the MSCs is also co-administered into the nucleus pulposus or annulus fibrosus as a therapeutic agent. If this matrix has suitable mechanical properties, it can be used to restore the height of the disc space that was lost during the degradation process. The cells may be injected at the same time or concurrently with the matrix in the targeted area of the disc.

The volume of aspirated bone marrow obtained to harvest the MSCs is preferably between about 5 cc to about 100 cc. This volume is then used during the concentration process to concentrate the MSCs.

When centrifugation is selected, the methods disclosed by Connolly et al. can be used. Incorporated by reference in its entirety is *Development of an Osteogenic Bone Marrow Preparation*, JBJS 71-A (No. 5) (June 1989). In this rabbit study, Connolly reported that centrifugation of 7-10 ml of bone marrow yielded an average of $3.6 \times 10^6$ nucleated cells per milliliter in final cell suspension.

When the cells are concentrated using the centrifugation process, they are deliverable to the disc in a pellet form in suspension. In another embodiment, the cells are delivered using a carrier. The carrier can comprise, or can be selected from, the group consisting of beads, microspheres, nanospheres, hydrogels, gels, polymers, ceramics, collagen and platelet gels.

The carrier, in solid or fluid form, can carry the cells in several different ways. The cells can be embedded, encapsulated, suspended or attached to the surface of the carrier. In one embodiment, the carrier encapsulates the cells, provides nutrients, and protects the cells when they are delivered inside the disc. After a period of time inside the disc, the carrier degrades and releases the cells. Specific types of the various carriers are described below.

In some embodiments, the mesenchymal stem cells are provided in a sustained release device (i.e., sustained delivery device). The administered formulation can comprise the sustained release device. The sustained release device is adapted to remain within the disc for a prolonged period and slowly release the mesenchymal stem cells contained therein to the surrounding environment. This mode of delivery allows the mesenchymal stem cells to remain in therapeutically effective amounts within the disc for a prolonged period. One or more additional therapeutic agents can also be delivered by a sustained delivery device.

Synthetic scaffolds, such as fumaric-acid based scaffolds, have been designed and tailored to allow for attraction of certain cells and to provide direction for the cells to differentiate in desired areas. The cells can also be embedded in the scaffold and then injected into the target area without affecting the viability or proliferation of the cells. After implantation of the fumaric-acid based scaffold, it degrades over time and no further surgery is necessary to remove the scaffold.

Carriers can also comprise hydrogels. The cells are encapsulated in the polymer chains of the hydrogel after gelation. Hydrogels can be delivered in a minimally invasive manner, such as injection to the target area. The hydrogel is also resorbed by the body. Hydrogel properties such as degradation time, cell adhesion behavior and spatial accumulation of extracellular matrix can be altered through chemical and processing modifications.

Hydrogels suitable for use in the present invention include water-containing gels, i.e., polymers characterized by hydrophilicity and insolubility in water. See, for instance, "Hydrogels", pages 458-459, in *Concise Encyclopedia of Polymer Science and Engineering*, Eds. Mark et al., Wiley and Sons (1990), the disclosure of which is incorporated herein by reference in its entirety. Although their use is optional in the present invention, the inclusion of hydrogels can be highly advantageous since they tend to possess a number of desirable qualities. By virtue of their hydrophilic, water-containing nature, hydrogels can house viable cells, such as mesenchymal stem cells, and can assist with load bearing capabilities of the disc.

In one embodiment, the hydrogel is a fine, powdery synthetic hydrogel. Suitable hydrogels exhibit an optimal combination of properties such as compatibility with the matrix polymer of choice, and biocompatability. The hydrogel can include any one or more of the following: polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), and sulfonated polymers.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

In accordance with the present invention, there is provided a method of treating degenerative disc disease in an intervertebral disc having a nucleus pulposus, comprising administering autologous uncultured mesenchymal stem cells into a degenerated intervertebral disc.

In one embodiment, the autologous mesenchymal stem cells are harvested before they are administered into the disc.

In accordance with one aspect of the invention, the mesenchymal stem cells can be delivered into the disc space with at least one (an) additional therapeutic agent, such as an agent to aid in the proliferation and differentiation of the cells. There can be, for example, one additional therapeutic agent (i.e., a second therapeutic agent) or there can be multiple additional therapeutic agents (e.g., second and third therapeutic agents). The additional therapeutic agent may be delivered simultaneously with the mesenchymal stem cells. In another embodiment, the additional therapeutic agent is delivered after administering the mesenchymal stem cells to the disc. In yet another, the additional therapeutic agent is administered first, i.e., prior to administering the mesenchymal stem cells to the disc.

The same carrier may also be used to deliver the cells and the additional therapeutic agent. In some embodiments, the cells are located on the surface of the carrier and the additional therapeutic agent is placed inside the carrier. In other embodiments, the cells and the additional therapeutic agent may be delivered using different carriers.

Other additional therapeutic agents which may be added to the disc include, but are not limited to: vitamins and other nutritional supplements; hormones; glycoproteins; fibronectin; peptides and proteins; carbohydrates (simple and/or complex); proteoglycans; oligonucleotides (sense and/or antisense DNA and/or RNA); bone morphogenetic proteins (BMPs); differentiation factors; antibodies (for example, antibodies to infectious agents, tumors, drugs or hormones); gene therapy reagents; and anti-cancer agents. Genetically altered cells and/or other cells may also be included in the matrix of this invention. If desired, substances such as pain killers (i.e., analgesics) and narcotics may also be admixed with the carrier for delivery and release to the disc space.

In some embodiments, growth factors are additional therapeutic agents. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4, members of the platelet-derived growth factor (PDGF) family, including PDGF-AB, PDGF-BB and PDGF-AA; EGFs, members of the insulin-like growth factor (IGF) family, including IGF-I and -II; the TGF-β superfamily, including TGF-β1, 2 and 3 (including MP-52), osteoid-inducing factor (OIF), angiogenin(s), endothelins, hepatocyte growth factor and keratinocyte growth factor; members of the bone morphogenetic proteins (BMPs) BMP-1, BMP-3, BMP-2, OP-1, BMP-2A, BMP-2B, BMP-4, BMP-7 and BMP-14; HBGF-1 and HBGF-2; growth differentiation factors (GDFs), members of the hedgehog family of proteins, including indian, sonic and desert hedgehog; ADMP-1; GDF-5; and members of the colony-stimulating factor (CSF) family, including CSF-1, G-CSF, and GM-CSF; and isoforms thereof. The growth factor can be autologous such as those included in platelet rich plasma or obtained commercially. In one embodiment, the growth factor is administered in an amount effective to repair disc tissue.

In some embodiments, the growth factor is selected from the group consisting of TGF-β, bFGF, and IGF-1. These growth factors are believed to promote regeneration of the nucleus pulposus, or stimulate proliferation and/or differentiation of chondrocytes, as well as extracellular matrix secretion. In one embodiment, the growth factor is TGF-β. More preferably, TGF-β is administered in an amount of between about 10 ng/ml and about 5000 ng/ml, for example, between about 50 ng/ml and about 500 ng/ml, e.g., between about 100 ng/ml and about 300 ng/ml.

In one embodiment, at least one of the additional therapeutic agents is TGF-β1. In one embodiment, another additional therapeutic agent is FGF.

In some embodiments, platelet concentrate is provided as an additional therapeutic agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the ECM, and because its fibrin matrix provides a suitable scaffold for new tissue growth.

Therefore, in accordance with the present invention, there is provided a method of treating degenerative disc disease in an intervertebral disc having a nucleus pulposus, comprising:
 a) administering autologous uncultured mesenchymal stem cells into the degenerating disc; and
 b) transdiscally administering at least one additional therapeutic agent into the degenerating disc.

For the purposes of the present invention, "transdiscal administration" includes, but is not limited to:
 a) injecting a formulation into the nucleus pulposus of a degenerating disc, such as a relatively intact degenerating disc;
 b) injecting a formulation into the annulus fibrosus of a degenerating disc, such as a relatively intact degenerating disc;
 c) providing a formulation in a patch attached to an outer wall of the annulus fibrosus,
 d) providing a formulation in a depot at a location outside but closely adjacent to an outer wall of the annulus fibrosus ("trans-annular administration"); and
 e) providing the formulation in a depot at a location outside but closely adjacent to an endplate of an adjacent vertebral body ("trans-endplate administration").

Also in accordance with the present invention, there is provided a formulation for treating degenerative disc disease, comprising:
 a) autologous uncultured mesenchymal stem cells; and
 b) at least one additional therapeutic agent, wherein the formulation is present in an amount suitable for administration into a degenerating disc.

Also in accordance with the present invention, there is provided a device for delivering a formulation for treating degenerative disc disease to the disc comprising:
 a) a chamber containing the formulation comprising autologous uncultured mesenchymal stem cells and at least one additional therapeutic agent; and
 b) a delivery port in fluid communication with the chamber and adapted to administer the formulation to the disc.

In some embodiments, the cells may be introduced (i.e., administered) into the nucleus pulposus or the annulus fibrosus depending on which extra-cellular matrix needs rebuilding. In other embodiments, the cells may be introduced into both regions of the disc. Specific therapeutic agents may be selected depending on the region of the disc where the cells are going to be delivered.

In some embodiments, the cells alone are administered (e.g., injected) into the disc through a needle, such as a small bore needle. Alternatively, the formulation can also be injected into the disc using the same small bore needle. In some embodiments, the needle has a bore of about 22 gauge or less, so that the possibilities of producing a herniation are mitigated. For example, the needle can have a bore of about 24 gauge or less, so that the possibilities of producing a herniation are even further mitigated.

If the volume of the direct injection of the cells or formulation is sufficiently high so as to cause a concern of overpressurizing the nucleus pulposus, then it is preferred that at least a portion of the nucleus pulposus be removed prior to administration (i.e., direct injection) of the mesenchymal stem cells. In some embodiments, the volume of removed nucleus pulposus is substantially similar to the volume of the formulation to be injected. For example, the volume of removed nucleus pulposus can be within about 80-120% of the volume of the formulation to be injected. In addition, this procedure has the added benefit of at least partially removing some degenerated disc from the patient.

When injecting the mesenchymal stem cells into the nucleus pulposus, it is desirable that the volume of drug (i.e., formulation of cells suspended in growth medium or a carrier) delivered be between about 0.5 ml and about 3.0 ml comprising cells suspended in growth medium or a carrier. When injected in these smaller quantities, it is believed that the added or replaced volume will not cause an appreciable pressure increase in the nucleus pulposus. Factors to consider when determining the volume of drug to be delivered include the size of the disc, the amount of disc removed and the concentration of the mesenchymal stem cells in the growth medium or carrier.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating degenerative disc disease in an intervertebral disc having a nucleus pulposus in a patient, comprising administering TGF-β and concentrated autologous uncultured mesenchymal stem cells from 7-10 ml of the patient's bone marrow into the degenerated intervertebral disc immediately following harvesting of the cells.

2. The method of claim 1, wherein the cells are concentrated yielding an average of $3.6 \times 10^6$ cells per mL in final cell suspension prior to being administered into the intervertebral disc.

3. The method of claim 2, wherein the cells are concentrated by centrifugation.

4. The method of claim 2, wherein the cells are concentrated by filtration.

5. The method of claim 1, wherein the cells are administered to the disc using a carrier, wherein the carrier is selected from the group consisting of beads, microspheres, nanospheres, hydrogels, gels, polymers, ceramics, collagen and platelet gels.

6. The method of claim 5, wherein the carrier comprises a hydrogel.

7. The method of claim 5, wherein the carrier comprises microspheres.

8. The method of claim 1, wherein said TGF-β is between about 10 ng/ml and about 5000 ng/ml TGF-β.

9. The method of claim 8, wherein the TGF-β and the cells are administered into the intervertebral disc using a carrier, wherein the carrier is selected from the group consisting of beads, microspheres, nanospheres, hydrogels, gels, polymers, ceramics, collagen and platelet gels.

10. The method of claim 8, wherein the TGF-β is administered simultaneously with administering the cells to the disc.

11. The method of claim 8, wherein the TGF-β is administered prior to administering the cells to the disc.

12. The method of claim 8, wherein the TGF-β is administered after administering the cells to the disc.

13. The method of claim 1, wherein the cells are administered into the intervertebral disc in a formulation with a final volume of between about 0.5 ml and about 3.0 ml.

14. The method of claim 13, wherein the cells are administered into the nucleus pulposus of the disc.

15. The method of claim 13, wherein the cells are administered into the annulus fibrosus of the disc.

16. The method of claim 13, wherein a portion of the nucleus pulposus is removed prior to administering the cells into the intervertebral disc.

17. The method of claim 13, wherein the cells are administered through a needle.

18. The method of claim 17, wherein the needle bore has a maximum gauge of about 24 gauge.

19. The method of claim 1, wherein the formulation is administered in an amount of less than 1 mL.

20. The method of claim 1, wherein the cells are provided intra-operatively to the patient following harvesting from the patient.

21. A method of treating degenerative disc disease in an intervertebral disc having a nucleus pulposus in a patient, comprising administering TGF-β and autologous uncultured mesenchymal stem cells from the patient's bone marrow into a degenerated intervertebral disc immediately following harvesting of the autologous uncultured mesenchymal stem cells in a formulation with a final volume of between about 0.5 mL and about 3.0 mL.

22. The method of claim 21, wherein the cells are concentrated yielding an average of $3.6 \times 10^6$ cells per mL in final cell suspension prior to being administered into the intervertebral disc.

23. The method of claim 22, wherein the cells are concentrated by centrifugation.

24. The method of claim 22, wherein the cells are concentrated by filtration.

25. The method of claim 21, wherein the cells are administered to the disc using a carrier, wherein the carrier is selected from the group consisting of beads, microspheres, nanospheres, hydrogels, gels, polymers, ceramics, collagen and platelet gels.

26. The method of claim 25, wherein the carrier comprises a hydrogel.

27. The method of claim 25, wherein the carrier comprises microspheres.

28. The method of claim 21, wherein said TGF-β is between about 10 ng/ml and about 5000 ng/ml TGF-β.

29. The method of claim 28, wherein the TGF-β and the cells are administered into the intervertebral disc using a carrier, wherein the carrier is selected from the group consisting of beads, microspheres, nanospheres, hydrogels, gels, polymers, ceramics, collagen and platelet gels.

30. The method of claim 28, wherein the TGF-β is administered simultaneously with administering the cells to the disc.

31. The method of claim 28, wherein the TGF-β is administered prior to administering the cells to the disc.

32. The method of claim 28, wherein the TGF-β is administered after administering the cells to the disc.

33. The method of claim 21, wherein the cells are administered into the nucleus pulposus of the disc.

34. The method of claim 21, wherein the cells are administered into the annulus fibrosus of the disc.

35. The method of claim 21, wherein a portion of the nucleus pulposus is removed prior to administering the cells into the intervertebral disc.

36. The method of claim 21, wherein the cells are administered through a needle.

37. The method of claim 36, wherein the needle bore has a maximum gauge of about 24 gauge.

38. The method of claim 21, wherein the formulation is administered in an amount of less than 1 mL.

39. The method of claim 21, wherein the cells are provided intra-operatively to the patient following harvesting from the patient.

* * * * *